Figure 1:
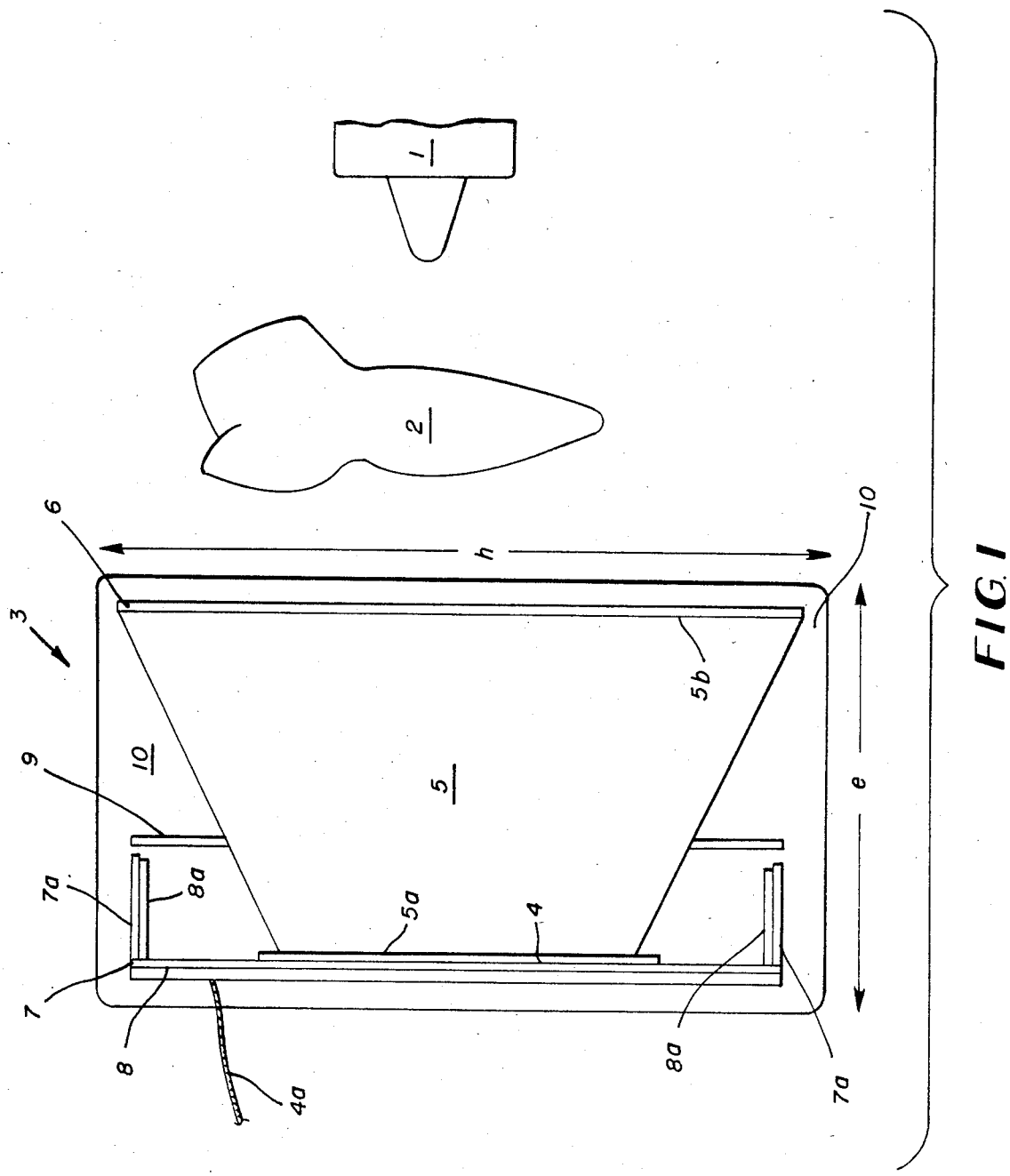

United States Patent [19]

Mouyen

[11] Patent Number: 4,593,400
[45] Date of Patent: Jun. 3, 1986

[54] APPARATUS FOR PROVIDING A DENTAL RADIOLOGICAL IMAGE AND INTRA-ORAL SENSOR USED THEREWITH

[76] Inventor: Francis Mouyen, 12, Avenue d'Occitanie, 31520 Ramoville-Saint-Agne, France

[21] Appl. No.: 621,237

[22] Filed: Jun. 15, 1984

[30] Foreign Application Priority Data

Jun. 16, 1983 [FR] France ............................ 83 10277

[51] Int. Cl.$^4$ ............................................. A61B 6/14
[52] U.S. Cl. .............................. 378/99; 250/213 VT; 378/191
[58] Field of Search ................ 378/191, 99; 250/213 VT

[56] References Cited

U.S. PATENT DOCUMENTS 3,051,166 8/1962 Hovnanian .
3,622,785 11/1971 Irwin et al. ........................... 378/99
4,160,997 7/1979 Schwartz .
4,228,356 10/1980 Cushman .
4,247,780 1/1981 Webber et al. .

FOREIGN PATENT DOCUMENTS 57-163885 10/1982 Japan .

Primary Examiner—Alfred E. Smith
Assistant Examiner—T. N. Grigsby
Attorney, Agent, or Firm—Birch, Stewart, Kolasch & Birch

[57] ABSTRACT

An apparatus for providing a dental radiological image on the monitor of a display system is provided by the present invention. Said apparatus comprises:
  an extraoral X-ray source;
  an intraoral sensor for the X-rays passing through a radiated tooth, said sensor being coaxial to the X-ray beam emerging from said tooth; and
  an extraoral electronic data processing unit connected to said sensor,
said sensor comprising a charge-coupled device and a screen, said screen being located between the charge-coupled device and the radiated tooth, and being provided on entry with a scintillator which converts the X-rays which have passed through the tooth into visible radiation, said screen being made of a layer of translucid material permeable to visible radiation, said translucid material being loaded with particles intended for preventing the passage of X-rays passing through said scintillator and which have not been converted into visible radiation by the scintillator,
  the diameter of each elemental part opposite the various constituents of the optical system organized according to the transmission of the dental image, i.e. scintillator, screen, charge-coupled device, being progressively increased for an optimization of the capacity of resolution of pixels (picture elements) in the charge-coupled device, and of the reduction of the moiré effect;
  said screen comprising reducing optical fibers loaded with metallic oxide particles intended to absorb the X-ray energy which has not been converted by the scintillator; and
  said intraoral sensor comprising a microelectronic means for monitoring the charge-coupled device and for amplifying the output signal of the charge-coupled device.

16 Claims, 1 Drawing Figure

APPARATUS FOR PROVIDING A DENTAL RADIOLOGICAL IMAGE AND INTRA-ORAL SENSOR USED THEREWITH

The present invention relates to dental radiology, and more particularly to an apparatus for providing a dental radiological image on the monitor of a display system.

Major developments in electronical techniques in the past few years have allowed considerable improvements in the techniques of radiological examination of the human body. These improvements have provided reduction, for the patient as well as the operator, of the dose of exposure to X-rays, while improving the quality of the image of the radiated target.

However, dental exploratory techniques still utilize the traditional radiography. Conventionally, the tooth to be examined is positioned between an extraoral source of X-rays, and an intraoral radiographic film sensitive to the X-rays passing through the radiated tooth. The shape of the image generated on this film corresponds to the shadows cast by the constituents more or less opaque to X-rays in the tooth examined. Although such dental radiographic technique is most commonly used nowadays, its major drawback is the limitation of the number of exposures, due to the doses of X-rays it requires.

It is useful to underline that the new techniques of radiology have dealt more particularly with the intrinsic design of the sensor of the X-ray beam emerging from the radiated target in order to reduce the time of exposure to X-rays while improving the quality of the image of the radiographed target. Moreover, the image is obtained instantly, thus avoiding the film development processing in traditional dental radiography.

Yet, adapting such improved devices to dental radiology meets serious problems, for the sensor of the X-ray beam must abide by certain maximal dimensions to allow easy introduction in the mouth. particularly of the type allowing to provide a dental radiologic image on the monitor of a display system resides therefore in making the sensor of the X-ray beam emerging from the radiated tooth as thin as possible so that it can be fitted in the oral cavity behind all the teeth subject to examination.

The design of such a device has already been described and represented in the U.S. Pat. No. 4,160,997 (Schwartz) which provides a sensor which comprises a charge-coupled device, and a screen located before said charge-coupled device, said screen converting the X-rays emerging from the radiated tooth into rays whose wavelength is adequate to said charge-coupled device. The charge-coupled device having its highest output in the visible spectrum, said screen has a scintillator material deposited thereon which acts to convert X-rays into visible radiation. On account of its small dimensions, it is clear that a charge-coupled device can fit the required conditions for the realization of a compact intraoral sensor enabling to a notable reduction in the doses of exposure to X-rays while offering an image superior in quality. The characteristics and technical advantages of the charge-coupled device are known by those skilled in the art and will not be recalled in the present specification.

One of the major drawbacks of the intraoral sensor described in the U.S. Pat. No. 4,160,997 consists in its incapacity for filling its essential function, i.e. recording the X-ray beam emerging from the radiated tooth and providing output data subject to analysis by an electronic processing unit, so as to display the image of said tooth on the monitor of a display system. In order to understand why this intraoral sensor is not functional, it is useful to remember that a charge-coupled device offers the following particulars:

- its sensitive surface is too small to allow full collection of the X-rays of a beam emerging from a radiated tooth and Schwartz consequently proposes to provide his oral sensor with a screen enabling linear transmission;
- its sensitive surface deteriorates under the collision with X-rays whose energy is superior to 1 keV and Schwartz's screen proves incapable of sufficiently protecting said sensitive surface;
- the maximum distance between the electronic unit for the data processing of electric output informations provided by the charge-coupled device, and said charge-coupled device is 7 inches (20 cm) (maximum distance beyond which the output signal is too weak to be processed, whereas in Schwartz's intraoral sensor the electronic unit for the data processing of output informations is extraoral and is connected to the sensor by a cable longer than 7 inches.

As the result of a thorough research, the invention provides an apparatus for providing a dental radiological image on the monitor of a display system which obviates the aforementioned drawbacks. It is a further object of the invention to provide a functional apparatus with undeniable performance in quality reproduction of the dental image as well as in the reduction of the X-ray exposure dose.

In accordance with the invention, the apparatus comprises:

- an extraoral X-ray source,
- an intraoral sensor for the X-rays passing through the radiated tooth, said sensor being coaxial to the X-ray beam emerging from the tooth,
- and an extraoral electronic data processing unit connected to the sensor, said sensor comprising a charge-coupled device and a screen, said screen being located between the charge-coupled device and the radiated tooth, and being provided on the entry with a scintillator which converts the X-rays which have passed through the tooth into visible radiation.

Also in accordance with the invention:

(i) the diameter of each elemental part of the various constituents of the optical system organized according to the transmission of the dental image, i.e. scintillator, screen, charge-coupled device, is progressively increased for an optimization of the capacity of resolution of pixels (picture elements) in the charge coupled device, thus reducing the "moiré" effect;

(ii) said screen comprises reducing optical fibers loaded with metallic oxide particles intended to absorb the X-ray energy which has not been converted by the scintillator;

and (iii) said intraoral sensor further comprises a microelectronic means for monitoring the charge-coupled device and for amplifying the output signal of the charge-coupled device.

It will be clearly understood that the realization of the intraoral sensor of the invention such as described above is not limited to the mere association of a scintillator, a screen and a charge-coupled device, which obviously could not work; it is the novel design and combination of these three components which form an optical system specifically meant for dental radiology.

Thus, giving a progressive increase to the diameter of each of the elemental parts of the various constituents of the optical system according to the transmission of the dental image, avoids an overlapping effect of "emitting" elemental parts upon "receptive" elemental parts which increases the "moiré" effect. The "moiré" effect may be lowered by having the matrix pattern designed by the optical fibers on issue of the screen and the matrix pattern of the charge-coupled device superposed and crossing at an angle of 45°. The 45° value has been chosen for the angle because the lines of both matrix patterns cross at angles of 90° which cause a double "moiré" effect when superposed. It is thus aimed at having a large number of crystals from the scintillator opposite an optical fiber on entry of the screen that will be balanced with a great number of optical fibers issuing from the screen opposite each picture element of the sensitive face of the charge-coupled device. This balance can be obtained by using ca. 3–4 $\mu$diameter crystals for the scintillator, 9–14$\mu$ diameter optical fibers on entry of the screen, and 4.5–7$\mu$ diameter optical fibers on issue of the screen, and 23–34$\mu$ diameter pixels (picture elements) for the charge-coupled device.

Further, using reducing optical fibers whose reductive rate is approximately 2 allows the obtainment of between the entry and the issue of the screen, a reduced transmission of the dental image, which (i) increases the number of optical fibers opposite each elemental pixel in the charge-coupled device, (ii) conforms the dimensions of the sensitive face of the charge-coupled device to that of the entry surface of the screen (imposed by the dimensions of the X-ray beam emerging from a radiated tooth and corresponding to the dimensions of the latter), and (iii) multiplies by 4 the intensity of light/surface ratio and consequently allows a reduction of the X-ray exposure dose by the same ratio (4).

The optical fibers, preferably of stabilized glass with a low darkening coefficient for perfect visible light transparency, are advantageously loaded with metallic oxide particles whose atomic mass is superior by 50% to the atomic mass of silicium in which optical fibers are spun, in order to absorb fittingly the energy of X-rays which has not been converted by the scintillator. Said metallic oxide particles protect the charge-coupled device by obstructing the path of the X-rays rejected by said charge-coupled device. According to a further advantageous feature of the invention, said metallic oxide particles have a tetravalent chemical structure and a melting point superior to 1 500° C. which allows spinning of reducing optical fibers containing said particles to diameters ranging between 4.5 and 7$\mu$, corresponding to those of the optical fibers on issue of the screen.

The invention further provides the intraoral sensor of the invention, with a microelectronic means for monitoring the charge-coupled device, and for amplifying the output signal of the charge-coupled device. Said microelectronic means solves the problem of the transmission of electric data from the charge-coupled device at a distance superior to 7 inches (20 cm). To reach this aim, the amplification of the data is carried out which enables the transmission of an electric signal to the electronic data processing unit of the display system. However, positioning this microelectronic means in the intraoral sensor raises some problems inasmuch as its presence can increase the volume of the charge-coupled device as well as cause an increase of temperature of its components, generating heat around the device, which would immediately increase its noise. In order to overcome the difficulties due to the bulkiness of this microelectronic means, according to a particularly advantageous characteristic of this invention, it has been imagined (i) to withdraw the chip constituting the functional part of the charge-coupled device, and (ii) to stick its sensitive face opposite the visible rays on the optical fibers on issue of the screen, and the other face on a ceramic substrate on which the microelectronic means is disposed using the multilayer technique for the sake of miniaturization. It is therefore clearly understood that the volume occupied by the various constituents of the optical system along the direction of image propagation is reduced to its minimum. It is important to specify that miniaturization can only affect the thickness of the charge-coupled device, because (i) the overall thickness of the intraoral sensor must remain close to 17 mm (millimeters) to allow an easy introduction in the oral cavity, (ii) the thickness of the scintillator must be inferior to 100$\mu$ to limit the problem of optical diffusion and (iii) the thickness of the screen must abide by a limited minimal dimension to ensure sufficient reduction (ratio:2) allowing the adequacy between the surface of the radiated tooth and that of the chip.

To avoid heating of the microelectronic means, the components liable to increase in temperature are dissociated (viz. the components ensuring voltage adaptation) and displayed on lateral projections perpendicular to the ceramic substrate. This characteristic of the invention offers the major advantage of distancing the chip from the heating components and therefore lowers its noise. According to a particularly advantageous characteristic of the invention, which further limits the temperature raise in the heating electronic components, the electric power supply of the microelectronic means for monitoring and amplifying the output signal is synchronized with that of the X-ray generated for a period of time necessary to obtain one single image on the monitor of the display system on which it will be maintained for ulterior exploratory study. This limited time allowed for the energy supply, experimentally determined to a few hundredths of second, offers the double advantage of considerable restriction of the dose of exposure to X-rays as well as of the temperature rise in the heating electronic components, so that miniaturization of the intraoral sensor might be achieved through the insertion of the microelectronic means in said intraoral sensor.

According to a further preferred embodiment of the invention, the scintillator is coated on the optical fibers on entry of said screen by depositing layers of crystals with a constant granulometry of 3–4$\mu$. The overall thickness of this deposit is inferior to 100$\mu$ in order to avoid the phenomenon of optical diffusion inside said scintillator. The emission wavelength of these crystals is comprised between 500 and 800 nm (nanometers) corresponding to the optimal range of response for the pixels (picture elements) of the chip. This mode of realization for the scintillator was conceived to improve the quality of the image reproduced.

Although the aspects of this invention which are considered to be novel are expressed in the appended claims, further details as to preferred practices and as to further features thereof may be most readily comprehended through reference to the following detailed description when taken in connection with the accompanying drawing, wherein FIG. 1 is a schematic cross-section of the apparatus.

Having reference to FIG. 1, the apparatus comprises:
an extraoral X-ray generator 1 for irradiating a tooth 2 set for example in the inferior jaw,
an intraoral sensor 3 for the X-rays that have passed through the tooth 2 behind which it is positioned,
and an extraoral electronic data processing unit, not represented, for the recording of output electrical informations from the intraoral sensor 3 to which it is linked by a flexible cable 4a, and for subsequently displaying the image of the tooth 2 on the monitor of a display system (not shown).

The invention essentially provides an intraoral sensor 3 which registers the full image of the radiated tooth 2 while sufficiently miniaturized to be easily positioned behind the tooth in the oral cavity. For a better comprehension of the invention, the sensor 3 has been represented on the drawing using a scale of 5.

Said sensor 3 with its coating material is shaped as a rectangular parallelepiped, ca. 30 mm high (h), 20 mm wide, and 17 mm maximum thick (c), to conciliate an easy introduction in the mouth with a full recording of the X-ray beam emerging from the tooth.

In accordance with the invention, the intraoral sensor 3 comprises the chip 4 of a charge-coupled device, said chip being stuck to one of the faces 5a of the truncated plane of a screen 5, said screen being shaped as a truncated pyramid whose base 5b is coated with a scintillator 6 which converts the X-ray emerging from the radiated tooth 2 into visible radiation which, as noticed above, will be better registered by said chip 4, especially when coating said base 5b with crystals whose wavelength ranges from 500 to 800 nm corresponding to the optimal range of response for chip 4.

The dimensions of the base 5b of said screen must provide a surface allowing full reception of the X-rays emerging from the tooth 2 while the dimensions of the truncated plane 5a must provide a surface small enough to be covered by the chip 4. Said screen 5 is made of reducing optical fibers (reduction rate ca 2) formed with stabilized glass loaded with metallic oxide particles.

Further to reducing the dental image between the entry 5b and the issue 5a of said screen, the optical fibers allow point by point the dental image between the scintillator 6 and the chip 4, and to lower the dose of exposure to X-rays, due to the reductive power of the fibers which increases the luminous intensity according to a rate proportional to the square of the reductive coefficient of the fibers.

The particles of metallic oxide loaded in the optical fibers must have an atomic mass superior by 50% to that of silicium so that they can absorb a reat part of the energy of the X-rays which have not been converted by the scintillator 6, thus ensuring a protective role for the chip 4. Further, the chemical structure of the chosen metallic oxide must have a four-valence outer shell while its melting point transmission of must be superior to 1500° C., in order to allow respectively chemical and physical compatibility with silicium, and to give a viscosity range enabling to spin optical fibers to diameters ranging from 4.5 to 7μ.

Thus, upon collision with the crystals of the scintillator 6, the X-rays passing through the tooth 2 emit light rays representing an image of the tooth 2 in the visible spectrum, said image being guided and shrunk point by point by the optical fibers of the screen 5 to the entry of the chip 4. In accordance with the invention, said chip has been withdrawn from its casing to be placed on a thin ceramic substrate 7. Said substrate is struck to the face of said chip opposite to that facing the screen 5. Said substrate further comprises a microelectronic means 8 for monitoring the chip 4 and for amplifying its output signal so as to transmit at the end of the flexible cable 4a, an electric signal to be processed by the electronic unit of the display system.

To avoid heating around the chip 4 caused by the temperature rise of a number of electronic components that tend to heat, viz. the components ensuring voltage adaptation, said components designated 8a, have been dissociated from the microelectronic means 8 and displayed on lateral projections 7a perpendicular to said ceramic substrate 7.

According to a further advantageous feature of the invention, a lead belt 9 whose plane is parallel to the base 5b of the truncated pyramid 5 is provided around the lateral faces of said truncated pyramid. Said lead belt 9 is located at a height equal to the two-thirds of the total height of the pyramid starting from the base 5b. Said lead belt ensures for the components located above (viz. the chip 4 and the microelectronic means 8) a protection from the X-rays which have not been converted by the scintillator 6 and which have a linear path through the thickness of said screen 5 located before the belt 9. Said thickness which represents the two thirds of the total thickness of the screens 5 (i.e. of the ⅔ of the height of the truncated pyramid) has been determined experimentally as the minimal thickness allowing sufficient X-ray absorption.

All the outer faces of the constituents described above (chip 4, screen 5, scintillator 6, ceramic substrate 7, microelectronic means 8 and lead belt 9) are advantageously embedded in a coating material 10, preferably a black polyurethane resin ensuring:

(i) a selective passage for specific wavelengths, which permits passage of the X-rays while preventing the passage of visible radiation external to the sensor 3 so as not to disturb the X-ray reception by the scintillator 6:

(ii) a low coefficient of thermal conduction for limiting the heating of the electronic components around the chip 4;

(iii) an electric insulation;

(iv) and a mechanical protection of the sensor against impacts.

According to a further advantageous feature of the invention, the sensor 3 will be placed in a throw-away aseptic pack (not shown), said pack being bio-compatible with the oral cavity.

In order to place the sensor 3 in the appropriate position for the reception of the beam of X-rays emerging from an irradiated tooth inside the mouth, said sensor 3 is movably and jointedly connected at the end of an arm (not shown) whose other end remains free to be positioned between two antagonist teeth.

It should be understood that the specific embodiments and practices described in connection with this specification have been presented by way of disclosure rather than limitation, and that various modifications, combinations and substitutions may be effected by those skilled in the art without departure either in spirit or scope from this invention in its broader aspects and as set forth in the appended claims.

What I claim is:

1. An apparatus for providing a dental radiological image on the monitor of a display system, said apparatus comprising:
an extraoral X-ray source;
an intraoral sensor for the X-rays passing through a radiated tooth, said sensor being coaxial to the X-ray beam emerging from said tooth; and
an extraoral electronic data processing unit connected to said sensor,
said sensor comprising a charge coupled device and a screen, said screen being located between the charge-coupled device and the radiated tooth, and being provided on entry with a scintillator which converts the X-rays which have passed through the tooth into visible radiation, said screen being made of a layer of translucid material permeable to visible radiation, and translucid material being loaded with particles intended for preventing the passage of X-rays passing through said scintillator and which have not been converted into visible radiation by the scintillator,
each elemental part of the various constituents of the optical system constituted of said scintillator, said screen, and said charge-coupled device organized according to the transmission of the dental image, having a diameter progressively increased for an optimization of the capacity of resolution of picture elements in the charge-coupled device, and of the reduction of the double moiré effect;
said screen comprising reducing optical fibers loaded with metallic oxide particles intended to absorb the X-ray energy which has not been converted by said scintillator; and
said intraoral sensor comprising a microelectronic means for monitoring the charge-coupled device and for amplifying the output signal of the charge-coupled device.

2. An apparatus as set forth in claim 1, wherein the matrix pattern designed by said optical fibers on issue of the screen and the matrix pattern of said charge-coupled device are superposed and cross at an angle of 45°.

3. An apparatus as set forth in claim 1, wherein the crystals of the scintillator have a 3–4$\mu$ diameter, said reducing optical fibers have a 9–14$\mu$ diameter on entry of the screen and a 4.5–7$\mu$ diameter on issue of said screen, and said picture elements of the charge-coupled device have a 23–34$\mu$ diameter.

4. An apparatus as set forth in claim 1, wherein the optical fibers of said screen are made of stabilized glass with a low darkening coefficient.

5. An apparatus as set forth in claim 1, wherein said charge-coupled device comprises a chip constituting its functional part, said chip being withdrawn from its casing and having its sensible face stuck on the optical fibers on issue of said screen and having its opposite face stuck on a ceramic substrate, said ceramic substrate further supporting said microelectronic means for monitoring the charge-coupled device and for amplifying the output signal of the charge-coupled device, said microelectronic means being disposed using the multi-layer technique.

6. An apparatus as set forth in claim 1, wherein said scintillator is coated on the optical fibers on entry of said screen by depositing layers of crystals with a constant granulometry of 3–4$\mu$, the deposit having an overall thickness inferior to 100$\mu$ in order to avoid the phenomena of optical diffusion, said deposit having an emmission wavelength ranging from 500 to 800 nm (nanometers) corresponding to the optimal range of response for the charge-coupled device.

7. An apparatus as set forth in claim 1, wherein the metallic oxide particles loading the optical fibers of said screen have an atomic mass superior by 50% to the atomic mass of silicium constituting the stabilized glass in which said optical fibers are spun, in order to increase the degree of absorbtion of the screen upon the X-rays which have not been converted into visible radiation by the scintillator and wherein said metallic oxide particles have a tetravalent chemical structure and a melting point superior to 1 500° C. which allows spinning of reducing optical fibers containing said particles to diameters of a few microns.

8. An apparatus as set forth in claim 5. wherein the electric power supply of the microelectronic means for monitoring the chip of the charge coupled device and for amplifying the output signal of said chip is synchronized with that of the X-ray generator for the minimum period of time necessary to obtain one single image on the monitor of the display chain on which said image will be maintained for ulterior exploratory study.

9. An apparatus as set forth in claim 7, wherein:
said screen, made of the reducing optical fibers, is shaped as a truncated pyramid whose top plane is parallel to the base;
said scintillator lies on said base of the pyramid and the sensible face of the chip is stuck on the truncated top plane of said pyramid; and
a lead belt whose plane is parallel to the base of the truncated pyramid projects from the lateral faces of said truncated pyramid, said lead belt being located at a height equal to the two-thirds of the total height of the pyramid starting from the base.

10. An apparatus as set forth in claim 8, wherein the components of the microelectronic means liable to raise the temperature around the chip are dissociated and displayed on lateral projections of the ceramic substrate, said projections being perpendicular to the remaining components stuck on the chip.

11. An apparatus as set forth in claim 10, wherein the outer faces of the constituents of the intraoral sensor for the X-rays emerging from a radiated tooth are embedded in a coating material ensuring:
(i) a selective passage for specific wavelengths, which permits the passage of the X-rays while preventing the passage of visible radiations external to the sensor so as not to disturb the X-ray reception by the scintillator;
(ii) a low coefficient of thermal conduction for limiting the heating of the electronic components located around the chip;
(iii) an electric insulation; and
(iv) a mechanical protection of the sensor against impacts.

12. An apparatus as set forth in claim 11, wherein the dimensions of the various constituents of said intraoral sensor for the X-ray beam emerging from a radiated tooth are such as:
the dimensions of said intraoral sensor allow easy introduction and withdrawing in and from the mouth of said sensor;
the dimensions of the base of the truncated pyramid-shaped screen on which the crystals of the scintillator are deposited allow reception on entry of the screen of the full image of the X-ray beam emerging from said radiated tooth;

the dimensions of the truncated plane of said pyramid-shaped screen on which is stuck the sensible face of said chip of said charge-coupled device allow to obtain on issue of the screen a dental image whose size is reduced enough to allow it to be registered by said sensible face of the chip; and the height of the truncated pyramid-shaped screen corresponds to the length of the optical fibers loaded with metallic oxide particles, and allows sufficient absorption of the energy of the X-rays which have not been converted into visible radiation by the scintillator, thus ensuring protection of the sensitive face of said chip.

13. An apparatus as set forth in claim 11, wherein said coating material for the outer faces of the various constituents of said intraoral sensor is black polyurethane resin.

14. An apparatus as set forth in claim 12, wherein the entry of the intraoral sensor is a 30 mm×0 mm rectangle which corresponds to the base of said truncated pyramid and wherein the thickness of said intraoral sensor is limited to 17 mm, which corresponds to the sum of the thickness of said scintillator, screen, chip, microelectronic means, and coating material.

15. An apparatus as set forth in claim 1, wherein said intraoral sensor is positioned in the mouth by means of a movable and jointed arm.

16. An apparatus as set forth in claim 1, wherein said intraoral sensor is placed in a throw-away aseptic pack.

* * * * *